United States Patent
Duran

Patent Number: 5,947,982
Date of Patent: Sep. 7, 1999

[54] SUTURE-PASSING FORCEPS

[75] Inventor: John S. Duran, Attleboro, Mass.

[73] Assignee: Smith & Nephew, Inc., Andover, Mass.

[21] Appl. No.: 08/832,061

[22] Filed: Apr. 2, 1997

[51] Int. Cl.[6] .................................................. A61B 17/04
[52] U.S. Cl. ........................ 606/139; 606/144; 606/139
[58] Field of Search ........................... 606/139, 144–148, 606/222, 223, 224

[56] References Cited

U.S. PATENT DOCUMENTS

| | | |
|---|---|---|
| 919,138 | 4/1909 | Drake et al. . |
| 1,037,864 | 9/1912 | Carlson et al. . |
| 1,635,066 | 7/1927 | Wells . |
| 1,815,725 | 7/1931 | Pilling et al. . |
| 2,610,631 | 9/1952 | Calicchio . |
| 2,880,728 | 4/1959 | Rights . |
| 3,013,559 | 12/1961 | Thomas . |
| 3,349,772 | 10/1967 | Rygg . |
| 3,470,875 | 10/1969 | Johnson et al. . |
| 3,638,653 | 2/1972 | Berry . |
| 3,752,516 | 8/1973 | Mumma ................................ 289/17 |
| 3,840,017 | 10/1974 | Violante . |
| 3,842,840 | 10/1974 | Schweizer . |
| 3,871,379 | 3/1975 | Clarke . |
| 3,901,244 | 8/1975 | Schweizer . |
| 3,946,740 | 3/1976 | Schweizer . |
| 4,161,951 | 7/1979 | Scanlan, Jr. . |
| 4,164,225 | 8/1979 | Johnson et al. . |
| 4,224,947 | 9/1980 | Fukuda . |
| 4,312,337 | 1/1982 | Donohue . |
| 4,493,323 | 1/1985 | Albright et al. . |
| 4,596,249 | 6/1986 | Freda et al. . |
| 4,602,635 | 7/1986 | Mulhollan et al. ................. 128/334 R |
| 4,621,640 | 11/1986 | Mulhollan et al. ..................... 128/340 |
| 4,641,652 | 2/1987 | Hutterer et al. ..................... 128/334 R |
| 4,643,178 | 2/1987 | Nastari et al. ..................... 128/92 YD |
| 4,779,616 | 10/1988 | Johnson ............................. 128/334 R |
| 4,781,190 | 11/1988 | Lee ..................................... 128/334 R |
| 4,890,615 | 1/1990 | Caspari et al. .......................... 128/340 |
| 4,923,461 | 5/1990 | Caspari et al. .......................... 606/146 |
| 4,957,498 | 9/1990 | Caspari et al. .......................... 606/146 |
| 4,961,741 | 10/1990 | Hayhurst ................................ 606/139 |
| 5,084,058 | 1/1992 | Li ........................................... 606/148 |
| 5,087,263 | 2/1992 | Li ........................................... 606/148 |
| 5,100,415 | 3/1992 | Hayhurst ................................ 606/139 |
| 5,100,418 | 3/1992 | Yoon et al. ............................. 606/139 |
| 5,100,421 | 3/1992 | Christoudias .......................... 606/147 |
| 5,133,723 | 7/1992 | Li et al. .................................. 606/148 |
| 5,149,329 | 9/1992 | Richardson ............................. 604/272 |
| 5,163,946 | 11/1992 | Li ........................................... 606/148 |
| 5,176,691 | 1/1993 | Pierce .................................... 606/148 |
| 5,181,919 | 1/1993 | Bergman et al. ...................... 606/144 |
| 5,192,287 | 3/1993 | Fournier et al. ....................... 606/139 |
| 5,201,744 | 4/1993 | Jones ..................................... 606/148 |
| 5,217,471 | 6/1993 | Burkhart ................................ 606/148 |
| 5,222,508 | 6/1993 | Contarini ............................... 128/898 |
| 5,234,443 | 8/1993 | Phan et al. ............................. 606/148 |
| 5,234,444 | 8/1993 | Christoudias .......................... 606/148 |
| 5,250,054 | 10/1993 | Li ........................................... 606/148 |
| 5,250,055 | 10/1993 | Moore et al. .......................... 606/148 |
| 5,257,637 | 11/1993 | El Gazayerli .......................... 128/898 |
| 5,261,917 | 11/1993 | Hasson et al. ......................... 606/139 |
| 5,269,791 | 12/1993 | Mayzels et al. ....................... 606/148 |
| 5,281,234 | 1/1994 | Wilk et al. ............................. 606/139 |
| 5,318,577 | 6/1994 | Li . |
| 5,397,325 | 3/1995 | Della Badia et al. . |
| 5,730,747 | 3/1998 | Ek ......................................... 606/148 |

FOREIGN PATENT DOCUMENTS

| | | |
|---|---|---|
| 0 778 004 A1 | 6/1997 | European Pat. Off. . |
| WO 96/39946 | 12/1996 | WIPO . |
| WO 96/39948 | 12/1996 | WIPO . |

*Primary Examiner*—Gary Jackson
*Attorney, Agent, or Firm*—Fish & Richardson P.C.

[57] ABSTRACT

A suture-passing forceps includes a suturing assembly having a member supported at a distal end of a support shaft, the member having a passage transverse to its length for supporting a suture needle in a suturing position at a selected angular orientation relative to the length of the member and configured to support the suture needle in a stowed position at an angle less than the selected angle of the suture needle in the suturing position.

26 Claims, 5 Drawing Sheets

SUTURE-PASSING FORCEPS

BACKGROUND OF THE INVENTION

The invention relates generally to suturing instruments for passing needled sutures.

An increasing number of surgical techniques are now performed arthroscopically to reduce trauma associated with large incisions generally required in open surgery. Arthroscopic surgery involves manipulating a surgical instrument from outside the body, while viewing the surgical site with an arthroscope, with both the instrument and arthroscope passed through small incisions or portals of the body. The surgical instrument is often placed through an appropriately sized cannula which extends from the portal to the surgical site to facilitate maneuvering of the surgical instrument.

Arthroscopic surgery is commonly performed at the joints of the body, for example, in repairing the meniscus of the knee or the rotator cuff and Bankart tendon in the shoulder. In such procedures, suture is used to stitch and reattach torn cartilage, tendons or ligaments to tissue or bone.

One approach for arthroscopically stitching a needled suture utilizes a suturing forceps having lower and upper jaws. The needled suture is positioned within the lower jaw and the jaws are closed by pivotal actuation to punch the needled suture from the lower jaw to the upper jaw and through the tissue being sutured.

SUMMARY OF THE INVENTION

The invention features a suture-passing forceps configured to support and deliver a needled suture to a surgical site while in a low profile configuration (e.g., with the jaws partially closed) and, upon arriving at the surgical site, support the needled suture in a larger profile, ready-for-use suturing position (e.g., with the jaws more fully open).

In a general aspect of the invention, the suture-passing forceps includes a suturing assembly having a member supported at a distal end of a support shaft, the member having a passage transverse to its length for supporting a suture needle in a suturing position at a selected angular orientation relative to the length of the member and configured to support the suture needle in a stowed position at an angle less than the selected angle of the suture needle in the suturing position.

Among other advantages, supporting the suture needle at the reduced angle allows the jaws of the suture-passing forceps to be closer together during delivery of the forceps to a surgical site. This reduced profile configuration makes the suture-passing forceps attractive for use in tight joints, such as in the shoulder and, in particular, in the repair of damaged tissue in the rotator cuff (e.g., Bankart tendon). In those surgical procedures requiring an introducing cannula, the reduced profile configuration of the forceps allows the use of a smaller cannula, thereby reducing the size of the incision and degree of trauma to the patient.

Embodiments of this aspect of the invention may include one or more of the following features.

The passage in the member includes an inclined wall which extends from a first opening having a diameter approximately that of the needle to a second, larger opening. The passage also includes a second wall, extending between the first and second openings and diametrically opposite the inclined wall, for supporting the needle in the suturing position. In one embodiment, the suture needle lies along the inclined wall in the stowed position, preferably retrograde, at an angle which reduces the overall profile of the suture assembly. Upon delivery to the surgical site, the needle is moved from the stowed position to the larger profile, suturing position with the needle supported in the first opening.

The member is a jaw pivotally attached to a second jaw having a retaining element, such as a hole, formed along an inner surface of the second jaw, to capture the tip of the suture needle in the stowed position. The retaining element protects the tip of the needle in the stowed position and secures the needle during delivery to the surgical site. The second jaw also includes a channel extending from a distal end of the second jaw to the hole. The channel serves as a guide for the needle as it is moved from the stowed position to the suturing position.

In another aspect of the invention, the above described suture-passing forceps is used to deliver a suture needle to a surgical site. The method of delivery includes passing the suture needle through the passage of the member and supporting the suture needle in the stowed position at an angle less than the selected angle of the suture needle in the suturing position. The suture-passing forceps is delivered to the surgical site with the needle in its stowed position, and, upon arriving at the site, the suture needle attached to the needle is pulled to move the needle into the suturing position where it is ready to be punched through the tissue to be sutured.

Embodiments of this aspect of the invention may include one or more of the following features.

The needle is supported within the passage in an inclined position such that pulling on the opposite end of the suture attached to the suture needle moves the suture needle from the inclined position to the suturing position where the needle is ready to be punched through the tissue to be sutured. The suture-passing forceps is delivered through a cannula which extends from a portal to the surgical site. Prior to passing the suture-passing forceps through the cannula, the jaw members are partially-closed, so that the distal end of the needle is captured and protected by the upper jaw. After passing the suture-passing forceps through the cannula, the jaw members are opened and the suture needle is moved to the suturing position. The tip of the suture needle is captured in the stowed position within a retaining element of the second jaw member. The retaining element protects the tip of the needle and prevents it from snagging or hooking tissue as it is being delivered to the surgical site.

Other features and advantages will become apparent from the following description, and from the claims.

DESCRIPTION OF THE PREFERRED EMBODIMENTS

Figure 1:
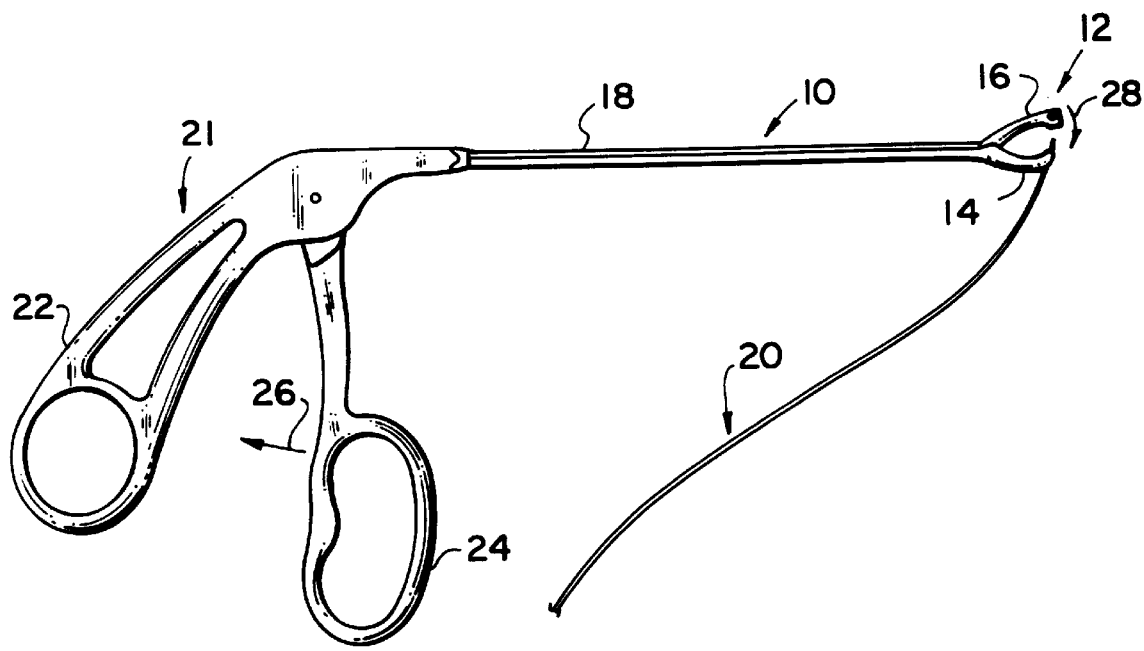
FIG. 1 shows the suture-passing forceps with a needled suture attached to a jaw of the forceps.

Referring to FIG. 1, a suture-passing forceps 10 for passing a needled suture 20 through tissue requiring repair (e.g., torn tissue in the rotator cuff) is shown. Forceps 10 includes a suturing assembly 12 having a lower stationary jaw 14 and an upper movable jaw 16, both of which are pivotally supported by a support shaft 18. A handle 21, connected to support shaft 18, is used to actuate upper jaw 16 towards and away from lower jaw 14 through a suitable linkage (not shown). Handle 21 includes a stationary thumb section 22 and a movable finger section 24. Movement of finger section 24 in the direction of arrow 26 closes jaws 14, 16 in the direction of arrow 28. The reverse motion of finger section 24 returns upper jaw 16 to its original, open position. A mechanism for actuating jaws 14, 16 towards and away from each other may include a pivot pin to hinge the jaws together. Alternatively, an arcuate lug and groove arrangement may be used, such as the one described in U.S. Pat. No. 4,712,545, issued to Honkanen, which is incorporated herein by reference.

When needled suture 20 is in a suturing position within lower jaw 14, the tissue to be attached is placed between jaws 14, 16 and hooked on the tip of the needle. Upon closing jaw 16, needled suture 20 is passed from lower jaw 14 to upper jaw 16 and through the damaged tissue where the needled suture it is captured in upper jaw 16. The suturing process can be repeated by reinserting needled suture 20 into lower jaw 14 where it is ready to be passed again through the tissue. A suture-passing forceps for performing this general operation is described in co-pending application U.S. Ser. No. 08/603,859, entitled "Suture Passing Forceps" which is incorporated herein by reference. As described therein, among the many advantages of this suture-passing forceps are passive capturing of the needle within the jaws of the forceps, one-step suture passing, one-handed suturing action and complete removal of the needled suture from the suturing assembly after suture passing.

As will be described in greater detail below, suturing assembly 12 is configured to support needled suture 20 in a stowed, non-suturing position (i.e., not ready to be punched) prior to delivering suture-passing forceps 10 to the surgical site. Once at the surgical site, suturing assembly 12 is also configured to support needled suture 20 in the suturing position where it is ready to be punched through tissue.

Figure 2:
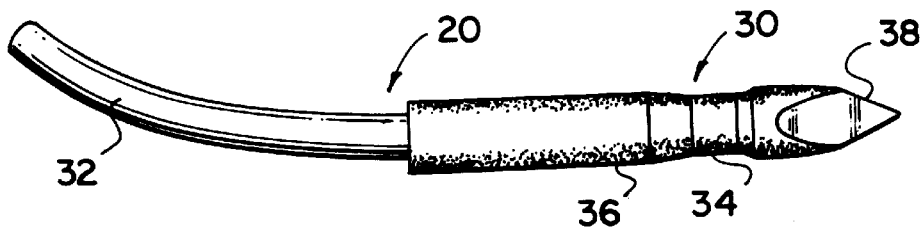
FIG. 2 shows a needled suture for use with the suture-passing forceps of FIG. 1.

Referring to FIG. 2, needled suture 20 includes a needle 30 co-axially aligned with suture thread 32 and attached (e.g., by crimping or clamping) to suture thread 32 at an attachment area 34. Needle 30 includes a substantially straight, tubular shaped body 36 and a pointed tip 38 for ease of passage through tissue. The length of needle 30 is typically less than about 0.5 inches and preferably about 0.3 inches. Suture thread 32 may be, e.g., #1 or #2 size sutures, monofilament or braided.

Figure 3:
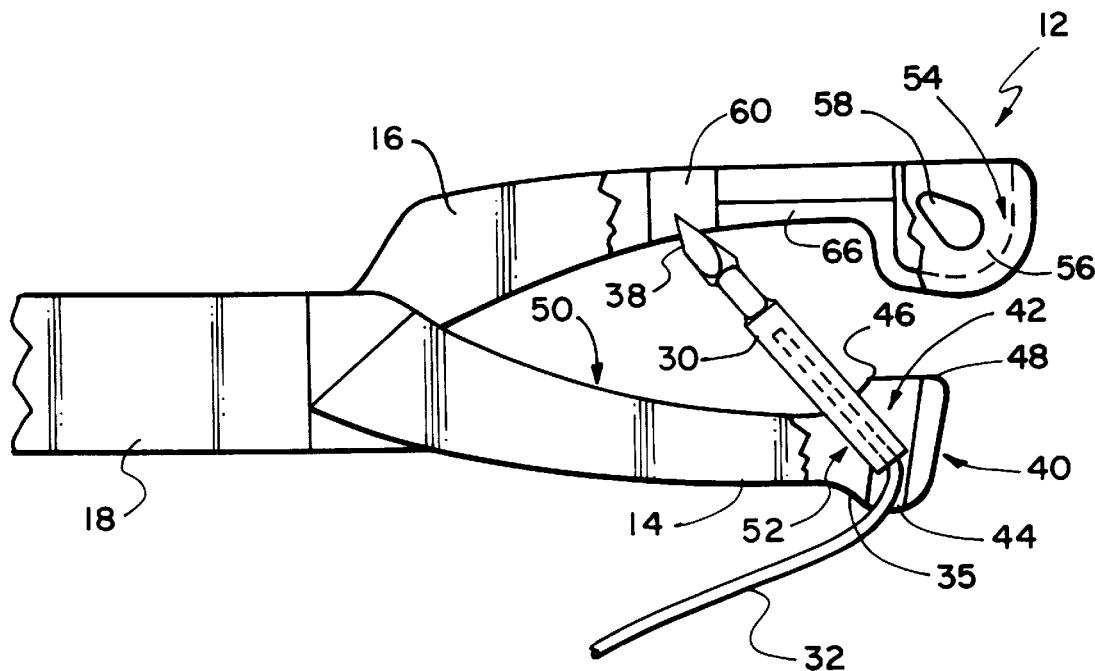
FIG. 3 is a partially cut-away side view of the suturing assembly of the suture-passing forceps of FIG. 1 with the jaws in a partially-closed position.
Figure 4:
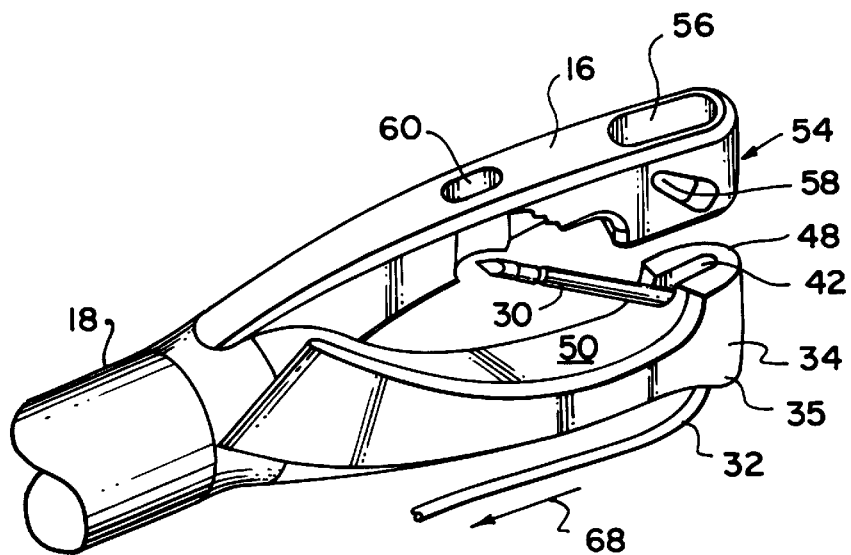
FIG. 4 is a partially cut-away perspective view of the suturing assembly of the suture-passing forceps of FIG. 3.

Referring to FIGS. 3 and 4, lower jaw 14 includes a needle holding region 40 for removably holding needle 30. Needle holding region 40 is defined by a suture passage 42 which extends through lower jaw 14 from a lower opening 44 to a larger, upper opening 46 at a face 48 of lower jaw 14. Upper opening 46 includes an inclined wall 52 extending from an edge of an inner contoured surface 50 to lower opening 44. Wall 52 serves to support body portion 36 of needle 30 in its inclined, non-suturing position. Upper opening 46 has a shape resembling an elongated groove that extends from approximately the center of face 48 towards surface 50 of jaw 14. Lower opening 44 has a diameter slightly larger than the diameter of body 36. Suture passage 42 also includes a forward wall 47 extending from lower opening 44 to upper opening 46 for supporting needle 30 in the suturing position. An axis 43 (FIG. 3) of suture passage 42 is slightly less than transverse (offset approximately 10°) to the plane of face 48 so that needle 30, in its suturing position, is better able to engage the tissue to be sutured. Outer surface 35 of lower jaw 14 is formed without sharp corners which might cut or fray suture 32 when, for reasons described below, suture 32 is pulled. Thus, in its suturing position, body portion 36 of needle 30 is firmly held in place by a friction fit within lower opening 44.

Upper jaw 16 includes a needle holding region 54 sized to firmly hold needle 30 when jaws 14, 16 are closed to punch sutured needle 20 through tissue. Needle holding region 54 is defined by a slotted opening 56 extending through upper jaw 16. The relative size of slotted opening 56 and the diameter of needle 30 in combination with the spring constant associated with the material of upper jaw 16 define the spring force with which needle 30 is held within slotted opening 56 when, in the punching operation, upper jaw 16 receives needled suture 20. Specific details relating to needle holding region 54 are provided in co-pending application U.S. Ser. No. 08/603,859. The holding force of upper jaw 16 on needle 30 is greater than the holding force of lower jaw 14 on the needle. This difference in holding force enables the needle to be passed from lower jaw 14 to upper jaw 16, as described below. Upper jaw 16 includes a window 58 through which needle 30 can be seen, enabling the user to confirm that needle 30 has been passed from lower jaw 14 to upper jaw 16.

A retaining hole 60 extends between an upper surface 62 and an inner contoured surface 64 of upper jaw 16 approximately midway along the length of upper jaw 16. Retaining hole captures tip 38 of needle 30 when needled suture 20 is in the stowed position (FIG. 3). A channel 66 formed along inner contoured surface 64 extends between retaining hole 60 and opening 56 and serves as a guide for needle 30 as it is moved from the stowed position to the suturing position, as described below.

Figure 5:
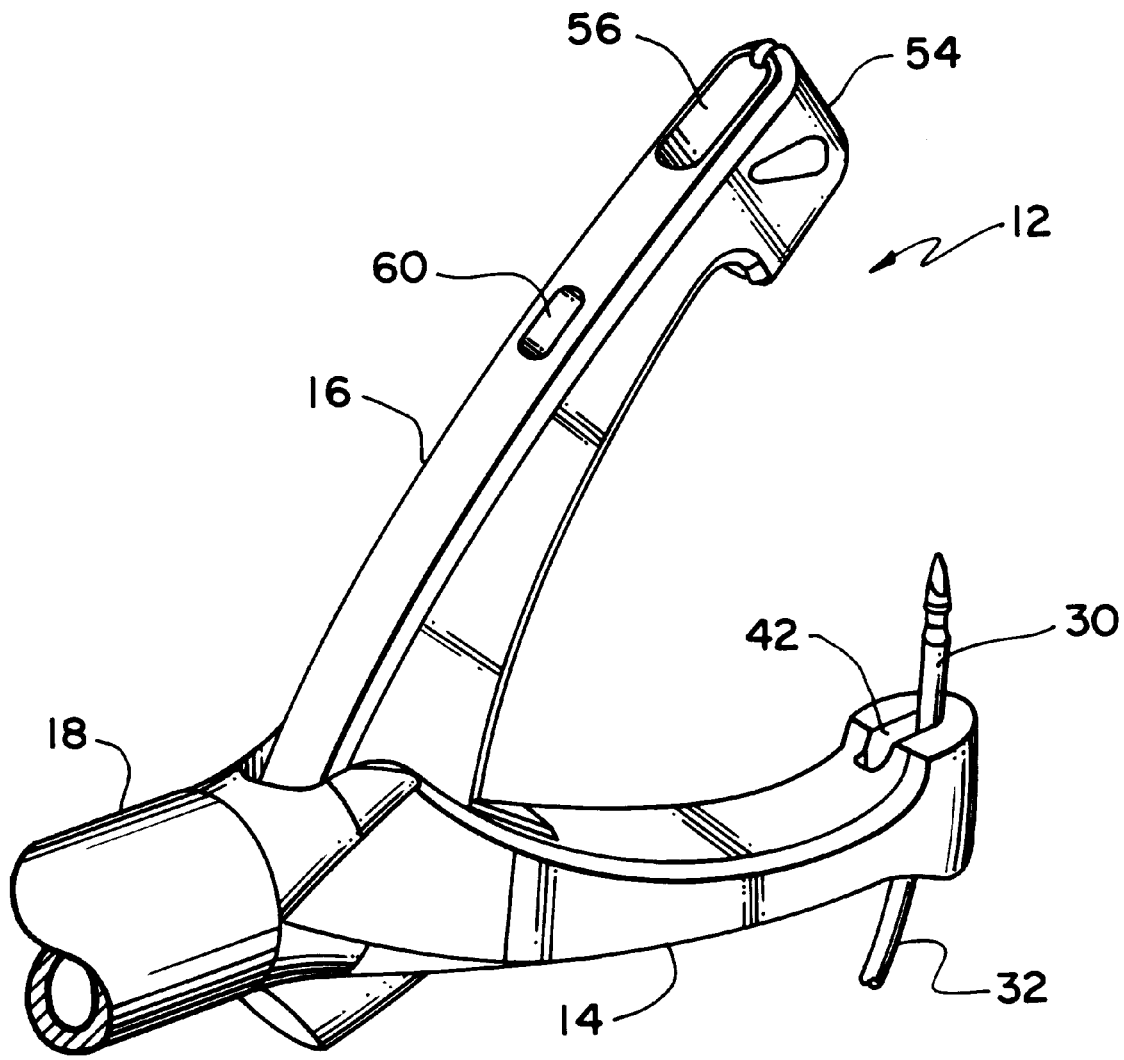
FIG. 5 is a perspective view of the suturing assembly of FIG. 1 with the jaws in an open position.

Referring to FIGS. 3–5, to move needled suture 20 from the inclined position to the suturing position, the proximal end of suture 32 is pulled in the direction of arrow 68 (FIG. 4) causing body portion 36 to slide against forward wall 47 and along inclined wall 52 into lower opening 44 where it is held in friction-fit in the upright suturing position. As body portion 36 moves into lower opening 44, the user opens upper jaw 16 so that needle tip 38 can slide from retaining hole 60 and along channel 62. Continuously pulling suture 32 causes needle 30 to "snap" in to lower opening 44 alerting the user that needled suture 20 is in the suturing position. Once in the suturing position, the user can open jaw 16 to its fully open position. Alternatively, upper jaw 16 can be fully opened prior to pulling suture 32. However, opening upper jaw 16 while pulling suture 32 maintains needle 30 within upper jaw 16 until just before the punching operation, minimizing any risk of catching or snagging surrounding tissue. Once needle 30 is in suturing position (FIG. 5), the tissue to be sutured is placed between jaws 14, 16 and needled suture 20 is punched through the tissue Referring to FIGS. 6A–6D, a procedure is shown in which a suture-passing forceps 10 is used to attach a suture anchor implanted within bone to tissue. It should be appreciated that an arthroscope or endoscope (not shown) is used to observe the procedure.

Figure 6A:
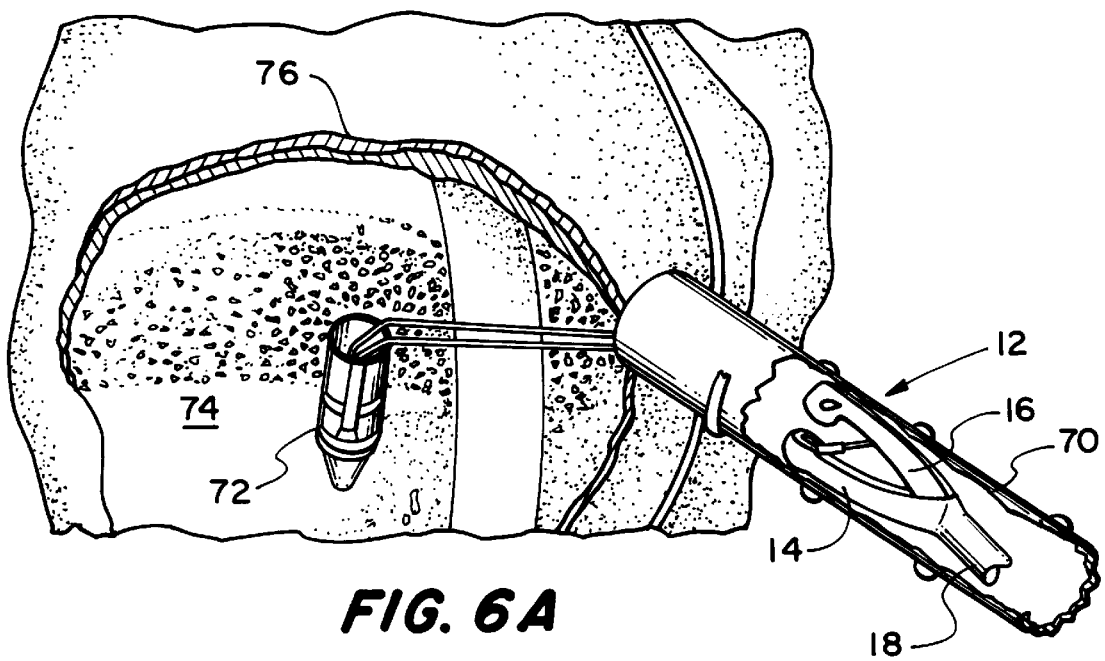
FIGS. 6A–6D illustrate the different stages of delivering and using the suture-passing forceps of FIG. 1.

A cannula 70 is inserted through a portal (not shown) and tissue at a joint. Cannula 70 has a diameter (e.g., 7 mm) less than a diameter normally required for passing suture forceps 10 having needled suture 20 in the upright, ready-for-suturing position. Because suturing assembly 12 is configured to support needled suture 20 in a stowed position, jaw 16 can be partially closed in a lower profile arrangement, allowing forceps 10 to be passed through a smaller cannula. In other words, suturing assembly 12 would not be able to fit through cannula 70 with jaw 16 in its fully open position. Needled suture 20 is threaded through an opening (not shown) of a suture anchor 72 implanted within a bone 72 and is then positioned in the stowed position within lower jaw 14. Jaw 16 is closed sufficiently to capture needle tip 36 within retaining hole 60 of upper jaw 16 so that suturing assembly 12 is in a low profile configuration. Forceps 10 is then advanced through cannula 70 to the surgical site (FIG. 6A).

Figure 6B:
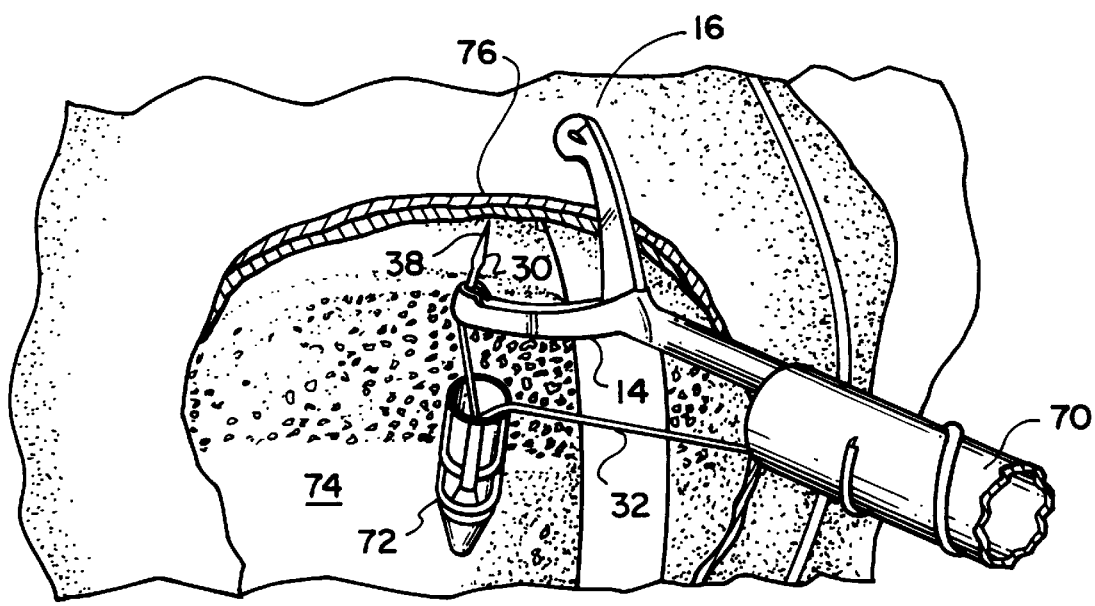
Figure 6C:
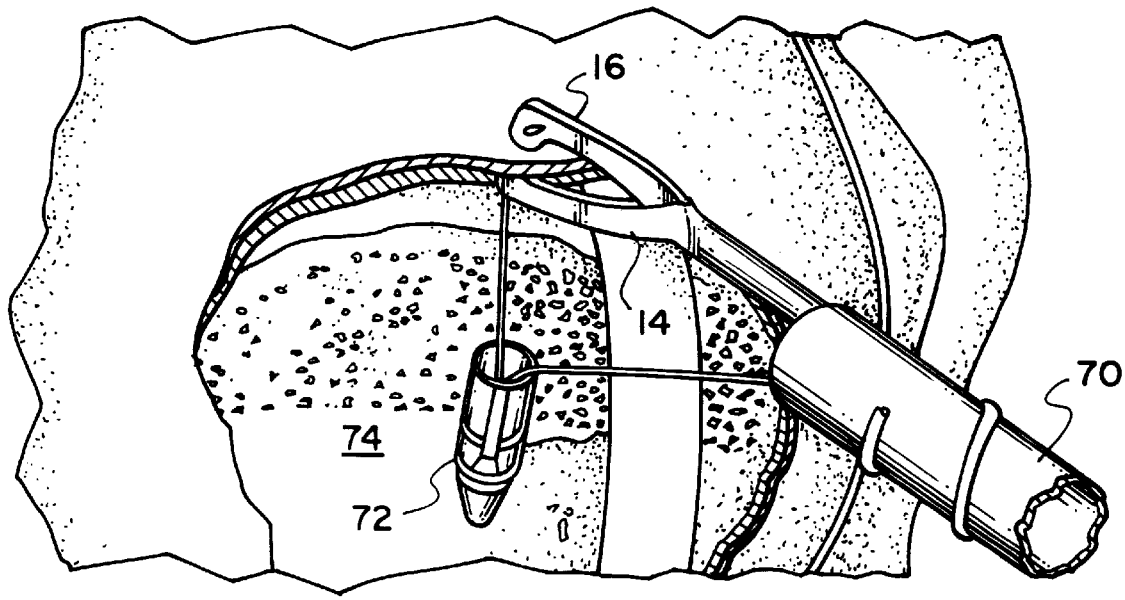
Figure 6D:
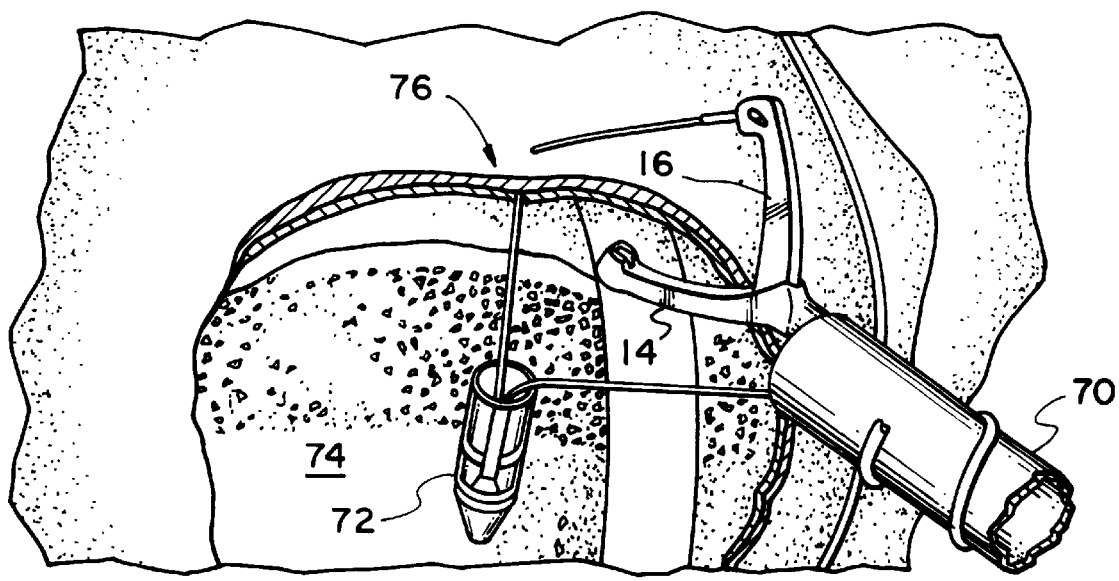

Once suturing assembly 12 is advanced beyond the distal end of cannula 70, upper jaw 16 is opened while suture 32 is pulled to move needle 30 into suturing position (FIG. 6B). Needle tip 38 is then hooked onto the tissue 76 to be sutured and jaw 16 closed to cause needle 30 to be passed from lower jaw 14 to upper jaw 16 and thus punched through tissue 76 (FIG. 6C). Jaw 16 is reopened to completely remove sutured needle 20 from lower jaw 14 (FIG. 6D). Jaw 16 is partially reclosed to allow suturing assembly 12 to be withdrawn back through cannula 70. Needled suture 20 can then be removed from upper jaw 16, placed again into lower jaw 14, and the procedure repeated.

Other embodiments are within the scope of the claims, such as the following alternative embodiments.

Although in the above-described embodiment, needle 30 is inclined retrograde (i.e, toward the pivot point of jaws 14, 16), in other embodiments, needle 30 may alternatively be inclined forward toward the distal end of the instrument. In this case, the length of upper jaw 16 may be extended with retaining hole 60 formed in this extended portion of the upper jaw.

Lower jaw 14 may also include a channel formed within inner recessed surface 50 of lower jaw 14. The channel would support needle 30 during delivery of suture-passing forceps 10. In this embodiment, needle 30 is not delivered in an inclined position; rather, the full length of needle 30 lies prostrate within the channel. Although in this embodiment suture opening 42 may not require an inclined wall 52, such a wall facilitates moving needle 30 into lower opening 44 and into suturing position.

While the illustrated embodiment shows suture opening 42 in stationary lower jaw 14, suture opening 42 could alternatively be disposed within movable upper jaw 16. Furthermore, both lower jaw 14 and upper jaw 16 can be configured to be movable jaws.

What is claimed is:

1. A suture-passing forceps for passing a suture needle, having suture attached thereto, through tissue at a surgical site, the suture-passing forceps comprising:
    a support shaft elongated along a longitudinal axis; and
    a suturing assembly disposed at a distal end of the support shaft and including:
    a member configured as a first jaw and supported by the support shaft, the member having a passage transverse to the length of the member for supporting the suture needle in a suturing position at a selected angular orientation inclined relative to the length of the member and for supporting the suture needle in a stowed position at an angle less than the selected angle of the suture needle in the suturing position.

2. The suture-passing forceps of claim 1 wherein the suture needle is disposed retrograde when in the stowed position.

3. The suture-passing forceps of claim 1 wherein the passage includes a wall inclined relative to the passage, the wall extending from a first opening having a diameter approximately that of the needle to a second opening, larger than the first opening.

4. The suture-passing forceps of claim 3 wherein the passage includes a second wall, extending between the first and second openings and diametrically opposite the inclined wall, for supporting the needle in the suturing position.

5. The suture-passing forceps of claim 1 wherein the suturing assembly further includes a second jaw pivotally attached to the support shaft for movement toward and away from the first jaw.

6. The suture-passing forceps of claim 1 wherein the second jaw includes a retaining element which captures a distal end of the suture needle in the inclined position.

7. The suture-passing forceps of claim 6 wherein the retaining element is a hole formed along an inner surface of the second jaw.

8. The suture-passing forceps of claim 1 wherein the passage includes a wall inclined relative to the passage, the wall extending from a first opening having a diameter approximately that of the needle to a second opening, larger than the first opening, the suture needle lying along the wall in the inclined position.

9. The suture-passing forceps of claim 1 wherein the second jaw includes a channel extending from a distal end of the second jaw to the groove.

10. A method of delivering a suture needle, having suture attached thereto, to a surgical site with suture-passing forceps having a first jaw disposed at a distal end of the forceps, the method comprising:
    passing the suture needle through a passage of the first jaw of the suture-passing forceps, the passage being transverse to the length of the first jaw to support the suture needle in a suturing position at a selected angular orientation relative to the length of the first jaw;
    supporting the suture needle in a stowed position at an angle less than the selected angle of the suture needle in the suturing position;
    delivering the suture-passing forceps to the surgical site;
    moving the suture needle from the stowed position into the suturing position of the passage in preparation for punching the suture needle through tissue to be sutured; and
    punching the suture needle through tissue to be sutured, by passing the suture needle from the first jaw to a second jaw pivotally attached to the first jaw for movement toward and away from the first jaw.

11. The method of claim 10 wherein the step of moving the suture needle into the suturing position includes pulling on the suture.

12. The method of claim 10 wherein the suture needle is disposed retrograde when in the stowed position.

13. The method of claim 10 wherein the suture needle, in the stowed position, is supported within the passage of the member in an inclined position.

14. The method of claim 10 wherein the delivering step includes passing the suture-passing forceps through a cannula which extends from a portal to the surgical site.

15. The method of claim 10 further comprising, prior to passing the suture-passing forceps through the cannula, actuating the first and second jaws to at least partially-close the jaws.

16. The method of claim 10 further comprising, prior to moving the suture needle to the suturing position and after passing the suture-passing forceps through the cannula, actuating the first and second jaws to an open position.

17. The method of claim 16 wherein the step of moving the suture needle into the suturing position includes pulling on the suture.

18. The method of claim 10 wherein the positioning step includes capturing a distal end of the suture needle in the stowed position within a retaining element of the second jaw.

19. A surgical apparatus comprising:

a suture needle having suture attached thereto;

a suture-passing forceps for passing the suture needle through tissue at a surgical site, the suture-passing forceps including:
  a support shaft elongated along a longitudinal axis; and
  a suturing assembly disposed at a distal end of the support shaft and including:
    first and second jaw members, each supported by the support shaft, the first jaw member having a passage transverse to the length of the first jaw member for supporting the suture needle in a suturing position at a selected angular orientation relative to the length of the member, the first jaw member configured to support the suture needle in a stowed position at an angle less than the selected angle of the suture needle in the suturing position.

20. A suture-passing apparatus for passing a suture needle, having suture attached thereto, through tissue at a surgical site, the suture-passing apparatus comprising:

a support shaft elongated along a longitudinal axis; and a suturing assembly disposed at a distal end of the support shaft and including:
  a member configured to be immovably supported by the support shaft, the member having a passage transverse to the length of the member for supporting the suture needle in a suturing position at a selected angular orientation relative to the length of the member, the member configured to support the needle in a stowed position at an angle less than the selected angle of the suture needle in the suturing position.

21. The suture-passing forceps of claim 20 wherein the suture needle is disposed retrograde when in the stowed position.

22. The suture-passing forceps of claim 20 wherein the passage includes a wall inclined relative to the passage, the wall extending from a first opening having a diameter approximately that of the needle to a second opening, larger than the first opening.

23. The suture-passing forceps of claim 22 wherein the passage includes a second wall, extending between the first and second openings and diametrically opposite the inclined wall, for supporting the needle in the suturing position.

24. The suture-passing forceps of claim 20 wherein the member is a first jaw configured to support the suture needle in an inclined position.

25. The suture-passing forceps of claim 24 wherein the suturing assembly further includes a second jaw pivotally attached to the support shaft for movement toward and away from the first jaw.

26. The suture-passing forceps of claim 25 wherein the passage includes a wall inclined relative to the passage, the wall extending from a first opening having a diameter approximately that of the needle to a second opening, larger than the first opening, the suture needle lying along the wall in the inclined position.

* * * * *